US00PP12859P2

(12) United States Plant Patent
Bradford

(10) Patent No.: US PP12,859 P2
(45) Date of Patent: Aug. 13, 2002

(54) CHERRY TREE NAMED 'GLENRED'

(76) Inventor: Lowell Glen Bradford, 12439 E. Savana Rd., Le Grand, CA (US) 95333

( * ) Notice: Subject to any disclaimer, the term of this patent is extended or adjusted under 35 U.S.C. 154(b) by 74 days.

(21) Appl. No.: 09/706,530

(22) Filed: Nov. 6, 2000

(51) Int. Cl.[7] ..... A01H 5/00
(52) U.S. Cl. ..... Plt./181
(58) Field of Search ..... Plt./181

*Primary Examiner*—Bruce R. Campell
*Assistant Examiner*—Michelle Kizilkaya

(57) ABSTRACT

The present invention relates to a cherry tree, *Prunus avium*, and more particularly to a new and distinct variety broadly characterized by a large size, vigorous, self-sterile but very productive and regular bearing tree. The fruit matures in the early season approximately in the second week in May under the ecological conditions described, with first picking on May 9, 2000. The fruit is uniformly large in size, very sweet in flavor, very firm and crisp in texture, entirely red in skin color, virtually non-doubling and somewhat resistant to skin cracking due to rain. The variety was a first generation cross using 'Tulare' (U.S. Plant Pat. No. 6,407) cherry as the seed parent and 'Brooks' (U.S. Plant Pat. No. 6,676) cherry as the selected pollen parent.

1 Drawing Sheet

BACKGROUND OF THE VARIETY

In a continuing effort to improve the quality of fresh market and shipping fruits, I, the inventor, typically hybridize a large number of nectarine, peach, apricot, plum and cherry seedlings each year. The present invention relates to a new and distinct variety of cherry tree, which has been denominated varietally as 'GLENRED' cherry. The present variety resulted from a seedling hybridized by me in 1992 and planted in a cultivated area of my experimental orchard near Le Grand, Calif. in Merced County (San Joaquin Valley). The variety was a first generation cross using 'Tulare' (U.S. Plant Pat. No. 6,407) cherry as the seed parent and 'Brooks' (U.S. Plant Pat. No. 6,676) cherry as the selected pollen parent. Subsequent to origination of the present variety of cherry tree, I asexually reproduced it by budding and grafting on Colt (U.S. Plant Pat. No. 4,059) cherry rootstock in the experimental orchard described above, and such reproduction of plant and fruit characteristics were true to the original plant in all respects.

The present variety is similar to its seed parent, 'Tulare', by producing early maturing fruit that is full red in skin color and virtually non-doubling, but is distinguished therefrom and an improvement thereon by being more vigorous in growth with a unique horizontal limb structure and by producing fruit that is larger in size, sweeter and milder in flavor, crispier in texture, and about 8 days earlier in maturing.

The present variety is similar to its pollen seed parent, 'Brooks', by producing early maturing fruit that is large, full red in skin color, and virtually non-doubling, but is distinguished therefrom and an improvement thereon by blooming about one week earlier, by possessing the natural horizontal limb structure and by producing fruit that is darker in flesh color, has a much longer stem, ripens about 4 days earlier and is considerably more resistant to skin cracking due to rain.

DRAWING

The accompanying color photograph displays a characteristic twig bearing leaves and a bunch of cherries, several fruits removed from the branch with the stems attached, several whole fruits detached from the stems to exhibit the skin color and form, a fruit sectioned transverse to the suture plane to reveal the flesh and fibers, and a few stones, all typical of the subject variety.

POMOLOGICAL CHARACTERISTICS

Referring now more specifically to the pomological characteristics of this new and distinct variety of cherry tree, the following has been observed under the ecological conditions prevailing near Le Grand, Merced County (San Joaquin Valley), Calif., and was developed at the state of shipping ripe on May 13, 2000. All major color code designations are by reference to the Inter-Society Color Council, National Bureau of Standards. Common color names are also used occasionally.

TREE

Size: Large, reaching a height of 14' [4.27 meters] by the 3rd year of growth on Colt rootstock.

Vigor: Very vigorous, responding aggressively to irrigation and fertilization. The variety should be grown on a standard commercial rootstock for production purposes.

Growth: Upright.

Form: A natural tendency to generate a central leader system if unpruned, but a vase shape may be obtained by pruning.

Tree structure: A unique proclivity for side limbs and fruit hangers to project at near right angles to main scaffolds, forming a horizontal limb pattern.

Trunk:

*Size.*—Large, reaching a maximum diameter of 4" [102 mm.] after 3 years of growth on Colt rootstock.

*Texture.*—Somewhat rough.

*Bark color.*—Dark grayish reddish brown [47. d.gy.rBr].

*Lenticels.*—Numerous. Color: Strong yellowish brownish [74. s.yBr]. Typical Size: ¼" to ½" [6.4–12.7 mm].

Branches:
*Size.*—Medium, typical of the species.
*Texture.*—Smooth on first year wood, increasing roughness with age.
*Color.*—1st Year Wood: Light yellow green [119.YG] with some Grayish red [19. gy.R] tinting from sunlight exposure. Older Wood: Dark brown [59. d.Br].
*Lenticels.*—Numerous, small. Color: Strong orange yellow [68. s.OY]. Typical Size: 1/16" to 1/8" [1.6–3.2 mm.].

Leaves:
*Size.*—Medium. Average Length: 6" [152 mm.]. Average Width: 2 5/16" [58.7 mm.].
*Thickness.*—Medium.
*Form.*—Elliptical.
*Apex.*—Acuminate.
*Base.*—Acute, typically about a 60 degree angle.
*Surface.*—Smooth.
*Color.*—Dorsal Surface: Dark grayish olive green [128. d.gy.OlG]. Ventral Surface: Moderate yellow green [120. m.YG].
*Margin.*—Finely serrate.
*Venation.*—Pinnately net veined.
*Petiole.*—Average Length: 1 3/4" [44.5 mm.]. Average Thickness: 3/32" [2.4 mm. ]. Color: Brilliant yellow green [116. brill.YG] blending into Dark red [16. d.R] where exposed to sunlight.
*Stipules.*—Ranging from none to 6 per leaf bud. Average Length: 1/2" [12.7 mm.].
*Glands.*—Predominately occur in alternately positioned pairs located on the stem about 3/8" [9.5 mm.] from basal leaf margin, rarely positioned oppositely, scarcely as numerous as 6 per leaf. Size: Large. Form: Oval to reniform. Color: Dark red [16. d.R].

Hardiness: Hardy with respect to typical central California winters.

Production: Very productive, thinning sometimes necessary.

Fertility: Self-sterile, cross-pollination required. Brooks is an acceptable pollinator for the latter part of the blooming period, but an earlier blooming cross-pollinator is necessary. Tulare is not interfertile with the present variety.

Bearing: Regular bearer, no alternate bearing observed.

Flower buds:
*Hardiness.*—Hardy with respect to central California winters.
*Diameter.*—Typically 3/8" [9.5 mm.] right before bloom.
*Length.*—Typically 3/4" [19.1 mm.] right before bloom.
*Form.*—Free.
*Surface.*—Smooth.
*Color.*—Grayish greenish yellow [105. gy.gY] with Moderate purplish pink [250. m.pPk] streaking.

Flowers: Perfect, complete, perigynous, usually a single pistil, typically twenty or more stamens, five sepal and petal locations alternately positioned.
*Blooming period.*—Early as compared to other varieties.
*Onset of bloom.*—Five percent on Mar. 14, 2000, about 1 week before 'Brooks' and 3 days before 'Tulare'.
*Duration of bloom.*—One to two weeks, dependent on ambient temperature.
*Bloom amount.*—Exceptionally abundant.
*Average diameter.*—1 1/2" [38.1 mm.].
*Color.*—White [263. White].
*Number of petals.*—Usually five.
*Petal shape.*—Obovate.
*Petal margin.*—Slightly undulate.
*Average petal length.*—5/8" [15.9 mm.].
*Average petal width.*—9/16" [14.3 mm.].
*Anther color.*—Brilliant yellow [83. brill.Y].
*Average pistil length.*—11/16" [17.5 mm.].
*Average stamen length.*—5/8" [15.9 mm.].
*Fragrance.*—Slight when nectar is present.

FRUIT

Maturity when described: Shipping ripe, May 13, 2000.

Date of first picking: May 9, 2000.

Date of last picking: May 18, 2000.

Tendency to double: Virtually none.

Size: Uniform, large.
*Average axial diameter.*—15/16" [23.8 mm.].
*Average cheek diameter.*—1 3/16" [30.2 mm.].
*Average suture diameter.*—1" [25.4 mm.].
*Typical weight.*—0.39 ounces [11 grams].

Form: Uniform, symmetrical and compressed toward the suture.
*Cheek plane form.*—Oblate.
*Longitudinal section form.*—Oval.
*Transverse section through diameter.*—Elliptical.

Suture: An inconspicuous Blackish red [21. blackish R] line and shallow trough from the base but discontinuing at the apex.

Ventral surface: Rounded.

Stem cavity: Flaring, circular, suture usually showing on one side.
*Depth.*—3/16" [4.8 mm.].
*Breadth.*—7/16" [11.1 mm.].

Base: Cuneate.

Apex: Truncate to slightly cuneate.

Pistil point: An inconspicuous dot depressed within the suture.

Stem: Long.
*Average length.*—1 7/8" [47.6 mm.].
*Average width.*—1/16" [1.6 mm.].
*Color.*—Light yellow green [119. l.YG] with some Grayish red [19. gy.R] tinting from sunlight.
*Attachment.*—Strong, but does not tear the skin when removed.

Skin:
*Thickness.*—Medium.
*Texture.*—Medium.
*Taste.*—Nonastringent.
*Tenacity.*—Tenacious to flesh.
*Tendency to crack.*—Slight after rain, not quite as resistant as the 'Tulare' but much more resistant than the 'Brooks'.
*Color.*—From Dark red [16. d.R] to Vivid dark red [17. v.d.R] over the entire surface.

Flesh:
*Color.*—Vivid dark red [17. v.d.R] toward the skin with Light grayish red [18. l.gy.R] streaking, Blackish red [21. blackish R] toward the stone.
*Surface of pit cavity.*—Short Blackish red [21. blackish R] fibers breaking when twisted away from the stone.
*Amygdalin.*—Moderate.
*Juice.*—Very abundant, rich, Vivid dark red [17. v.d.R].
*Texture.*—Firm, crisp.

*Fibers.*—Abundant, fine.
*Ripens.*—Slightly earlier near the stone.
*Flavor.*—Very sweet, somewhat low in acid, typically 16 to 22 brix.
*Aroma.*—Slight.
*Eating quality.*—Very best.

STONE

Type: Semi-freestone.
Form: Obovoid.
Length: ⅜" [9.5 mm.].
Width: ⅜" [9.5 mm.].
Breadth: 5/16" [7.9 mm.].
Base: Straight.
Apex: Rounded.
Sides: Equal.
Surface: Smooth.
Ridges: Two thin ridges along the ventral edge.
Color: Light yellowish brown [76. l.yBr] when dry.
Thickness of pit wall: 1/16" [1.6 mm.].
Tendency to split: None observed.
Kernel:
*Form.*—Oval.
*Taste.*—Bitter.
*Viable.*—Yes.
*Average width.*—¼" [6.4 mm.].
*Average length.*—3/16" [4.8 mm.].
*Skin color.*—Pale orange yellow [73. p.OY] with Light grayish yellowish brown [79. l.gy.yBr] veins when first removed from stone.
*Pellicle color.*—Light grayish yellowish brown [79. l.gy.yBr].
*Amygdalin.*—Abundant.

USE

Market: Fresh and long distance shipping.
Keeping quality: Fruit quality observed to remain in good condition in excess of 14 days in cold room at 36° Fahrenheit [2° Celsius].
Resistance to insects: No unusual susceptibilities noted.
Resistance to diseases: No unusual susceptibilities noted.

Although the new variety of cherry tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of cherry tree, substantially as illustrated and described, that is similar to both its seed parent, 'Tulare' (U.S. Plant Pat. No. 6,407), and its pollen parent, 'Brooks' (U.S. Plant Pat. No. 6,676), by producing early maturing fruit that is full red in skin color, very firm in texture and virtually non-doubling, but is distinguished from 'Tulare' and an improvement thereon by being more vigorous in growth and by producing fruit that is larger in size, sweeter and milder in flavor, crispier in texture, and about 8 days earlier in maturing, and is distinguished from 'Brooks' and an improvement thereon by blooming about 7 days earlier and by producing fruit that is darker in flesh color, has a much longer stem, ripens about 4 days earlier, and is considerably more resistant to skin cracking due to rain.

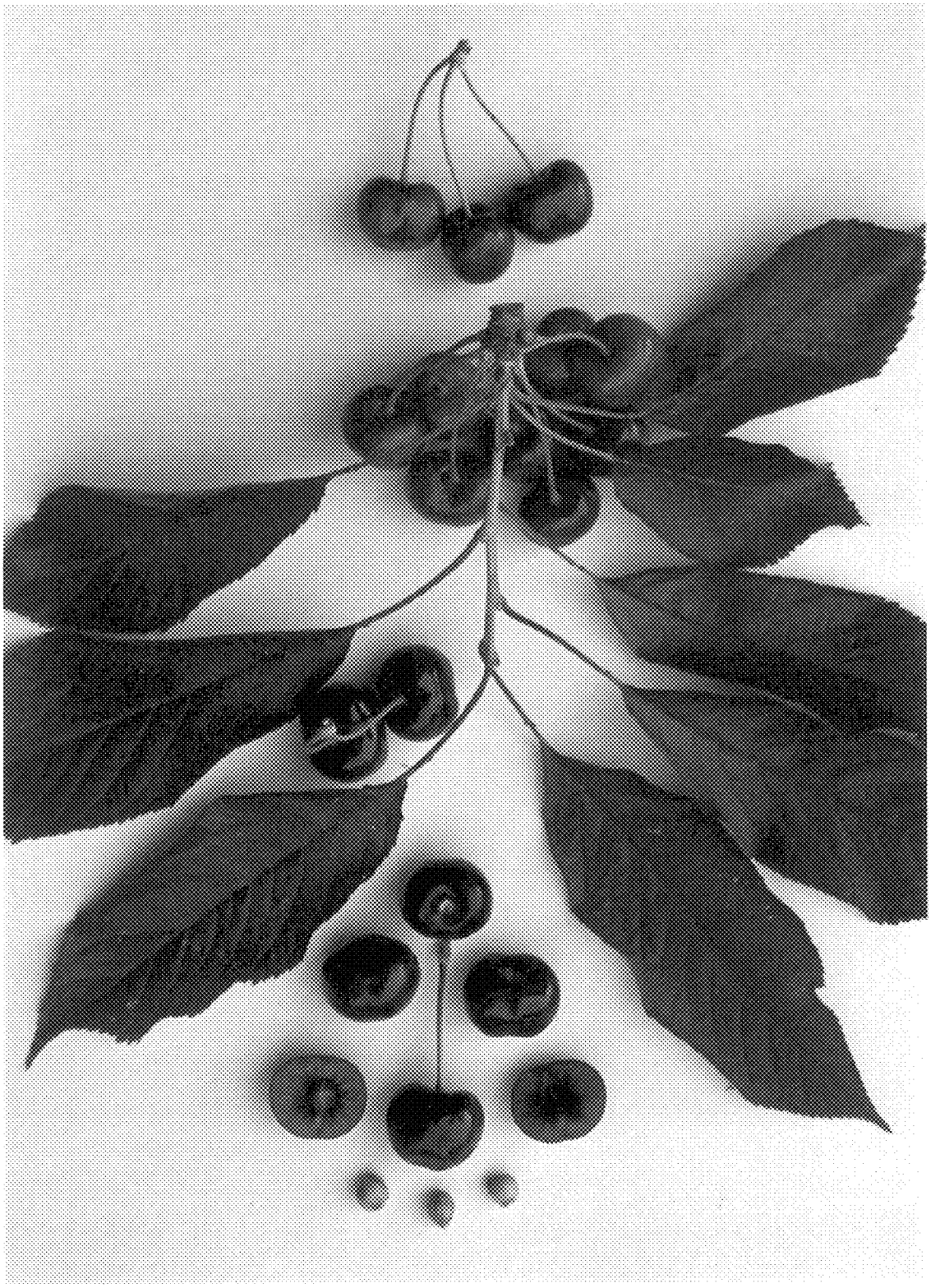

* * * * *